United States Patent
Baumgart et al.

(10) Patent No.: US 9,019,305 B2
(45) Date of Patent: Apr. 28, 2015

(54) METHOD OF VISUALIZATION OF CONTRAST INTENSITY CHANGE OVER TIME IN A DSA IMAGE

(75) Inventors: John Baumgart, Hoffman Estates, IL (US); Gary S. Martucci, Algonquin, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1085 days.

(21) Appl. No.: 12/624,193

(22) Filed: Nov. 23, 2009

(65) Prior Publication Data

US 2010/0259550 A1    Oct. 14, 2010

Related U.S. Application Data

(60) Provisional application No. 61/168,262, filed on Apr. 10, 2009.

(51) Int. Cl.
*G09G 5/00* (2006.01)
*A61B 6/00* (2006.01)

(52) U.S. Cl.
CPC ............... *A61B 6/504* (2013.01); *A61B 6/463* (2013.01); *A61B 6/467* (2013.01); *A61B 6/469* (2013.01); *A61B 6/481* (2013.01)

(58) Field of Classification Search
CPC ............ G06T 19/00; G06T 2207/10081; G06T 7/0081; G06T 2207/30101; A61B 2576/00; A61B 19/5244; A61B 6/504; G09B 23/285
USPC ................................... 345/589, 629
See application file for complete search history.

(56) References Cited

U.S. PATENT DOCUMENTS

| | | | |
|---|---|---|---|
| 2003/0004405 A1* | 1/2003 | Townsend et al. | 600/407 |
| 2006/0241465 A1* | 10/2006 | Huennekens et al. | 600/458 |
| 2008/0081998 A1* | 4/2008 | Pan et al. | 600/458 |
| 2008/0262346 A1* | 10/2008 | Assis et al. | 600/431 |
| 2009/0110252 A1* | 4/2009 | Baumgart et al. | 382/130 |
| 2009/0156927 A1* | 6/2009 | Schmidt | 600/420 |
| 2010/0030095 A1* | 2/2010 | Yu | 600/526 |

* cited by examiner

*Primary Examiner* — Devona Faulk
*Assistant Examiner* — Wynton S Jones (57) ABSTRACT

A system provides a display image enabling a user to visualize and compare blood flow characteristics over time at selected points in an angiographic X-ray image. A system and user interface enables user interaction with a medical vessel structure image to determine individual vessel blood flow characteristics. The system includes a user interface cursor control device and a display processor for generating data representing a single composite display image. The composite display image includes, a first image area showing a patient vessel structure and contrast agent flow through the patient vessel structure over a first period of time and a second image area showing a graph of contrast agent concentration in a particular portion of the vessel structure over a second period of time. The particular portion of the vessel structure is selected in response to user command using the cursor control device.

20 Claims, 6 Drawing Sheets

METHOD OF VISUALIZATION OF CONTRAST INTENSITY CHANGE OVER TIME IN A DSA IMAGE

This is a non-provisional application of provisional application Ser. No. 61/168,262 filed Apr. 10, 2009, by J. Baumgart et al.

FIELD OF THE INVENTION

This invention concerns a system and user interface enabling user interaction with a medical vessel structure image to determine individual vessel blood flow characteristics including contrast agent concentration in a particular portion of a vessel structure, for example.

BACKGROUND OF THE INVENTION

In order to study contrast agent flow, which is representative of blood flow through vessels in an angiography (e.g., Digitally Subtracted Angiography (DSA)) image sequence, it is useful to visualize the characteristics of flow over time at various points within an image while evaluating the need for treatment or the effectiveness of treatment. A DSA image sequence may be interpreted in known systems by determining contrast agent changes over time to indicate blood flow at particular points in an image. A known system may provide a static color image showing a single characteristic of a point in the image (e.g., time of contrast peak) but this fails to provide an indication of flow over time at different points in an image. A system according to invention principles addresses a need to provide a visual interpretation of blood flow at multiple different points in a composite image

SUMMARY OF THE INVENTION

A system provides a display image enabling a user to visualize and compare blood flow characteristics over time at selected points in an angiographic X-ray image. A system and user interface enables user interaction with a displayed medical vessel structure image to determine individual vessel blood flow characteristics. The system includes a user interface cursor control device and a display processor for generating data representing a single composite display image. The composite display image includes, a first image area showing a patient vessel structure and contrast agent flow through the patient vessel structure over a first period of time and a second image area showing a graph of contrast agent concentration in a particular portion of the vessel structure over a second period of time. The particular portion of the vessel structure is selected in response to user command using the cursor control device.

DETAILED DESCRIPTION OF THE INVENTION

A system provides a display image enabling a user to visualize and compare blood flow characteristics over time at selected points in an angiographic X-ray image. The system generates a graph of contrast agent intensity (representing blood flow) over time during display of a DSA (digitally subtracted angiography) image, in response to user selection of a point of interest in the DSA image. DSA involves acquiring a reference image (called a mask) which contains only static background detail and is acquired before injection of a contrast agent (e.g., an X-ray opaque dye) into patient anatomy. In order to remove static background detail from images, a mask image is subtracted from subsequent images acquired when a contrast agent is in patient blood which yields a clear picture of blood vessels filled with the contrast agent.

Figure 1:
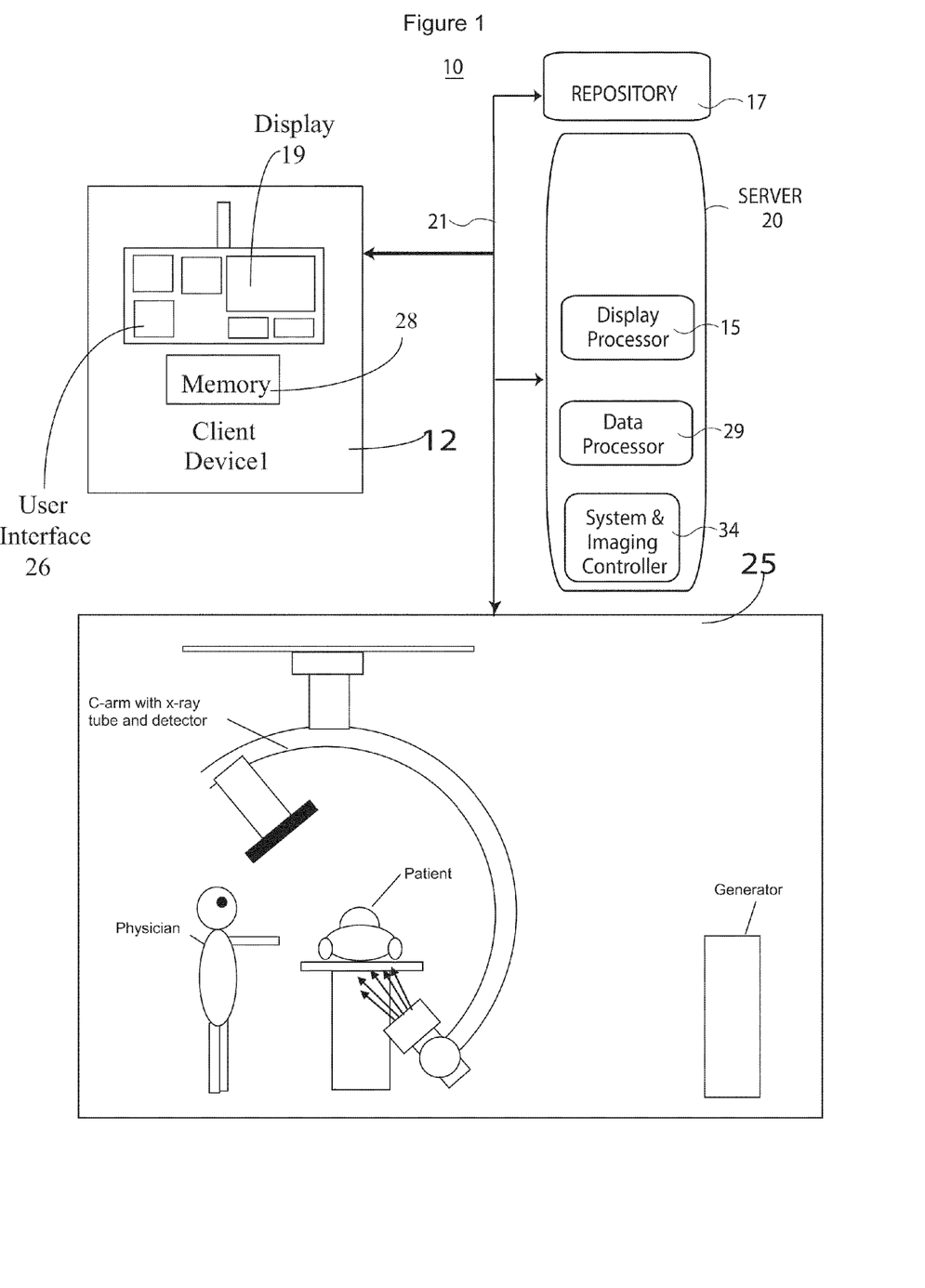
FIG. 1 shows a system and user interface enabling user interaction with a medical vessel structure image to determine individual vessel blood flow characteristics, according to invention principles.

FIG. 1 shows system and user interface 10 enabling user interaction with a medical vessel structure image to determine individual vessel blood flow characteristics. System 10 includes one or more processing devices (e.g., workstations or portable devices such as notebooks Personal Digital Assistants, phones) 12 that individually include a user interface control device 26 such as a keyboard, mouse, touchscreen, voice data entry and interpretation device and memory 28. System 10 also includes at least one repository 17, X-ray imaging modality system 25 (which in an alternative embodiment may comprise an MR (magnetic resonance), CT scan, or Ultra-sound system, for example) and server 20 intercommunicating via network 21. X-ray modality system 25 comprises a C-arm X-ray radiation source and detector device rotating about a patient table and an associated electrical generator for providing electrical power for the X-ray radiation system. Display processor 15 provides data representing display images comprising a Graphical User Interface (GUI) for presentation on processing device 12. The display images are generated in response to predetermined user (e.g., physician) specific preferences. At least one repository 17 stores medical image studies for multiple patients in DICOM compatible (or other) data format. A medical image study individually includes multiple image series of a patient anatomical portion which in turn individually include multiple images. Server 20 includes data processor 29 and system and imaging controller 34. Imaging controller 34 controls operation of imaging device 25 in response to user commands entered via user interface 26. In alternative arrangements, one or more of the units in server 20 may be located in device 12 or in another device connected to network 21.

Data processor 29 includes an image data subtraction system for processing images acquired by imaging device 25 to provide DSA images for use in Angiography (catheterization and stent manipulation) or other medical procedure to enhance vessel visualization. System and user interface 10 enables user interaction with a medical vessel structure image to determine individual vessel blood flow characteristics and includes a user interface cursor control device 26. Display processor 15 generates data representing a single composite display image for presentation on display 19. The single composite display image includes, first and second image areas. The first image area shows a patient vessel structure and contrast agent flow through the patient vessel structure over a first period of time. The second image area shows a graph of contrast agent concentration in a particular portion of the vessel structure over a second period of time. The graph is generated by data processor 29. The particular portion of the vessel structure is selected in response to user command using cursor control device 26. The first image area includes a visual marker identifying location in the vessel structure of the particular portion of the vessel structure.

Figure 2:
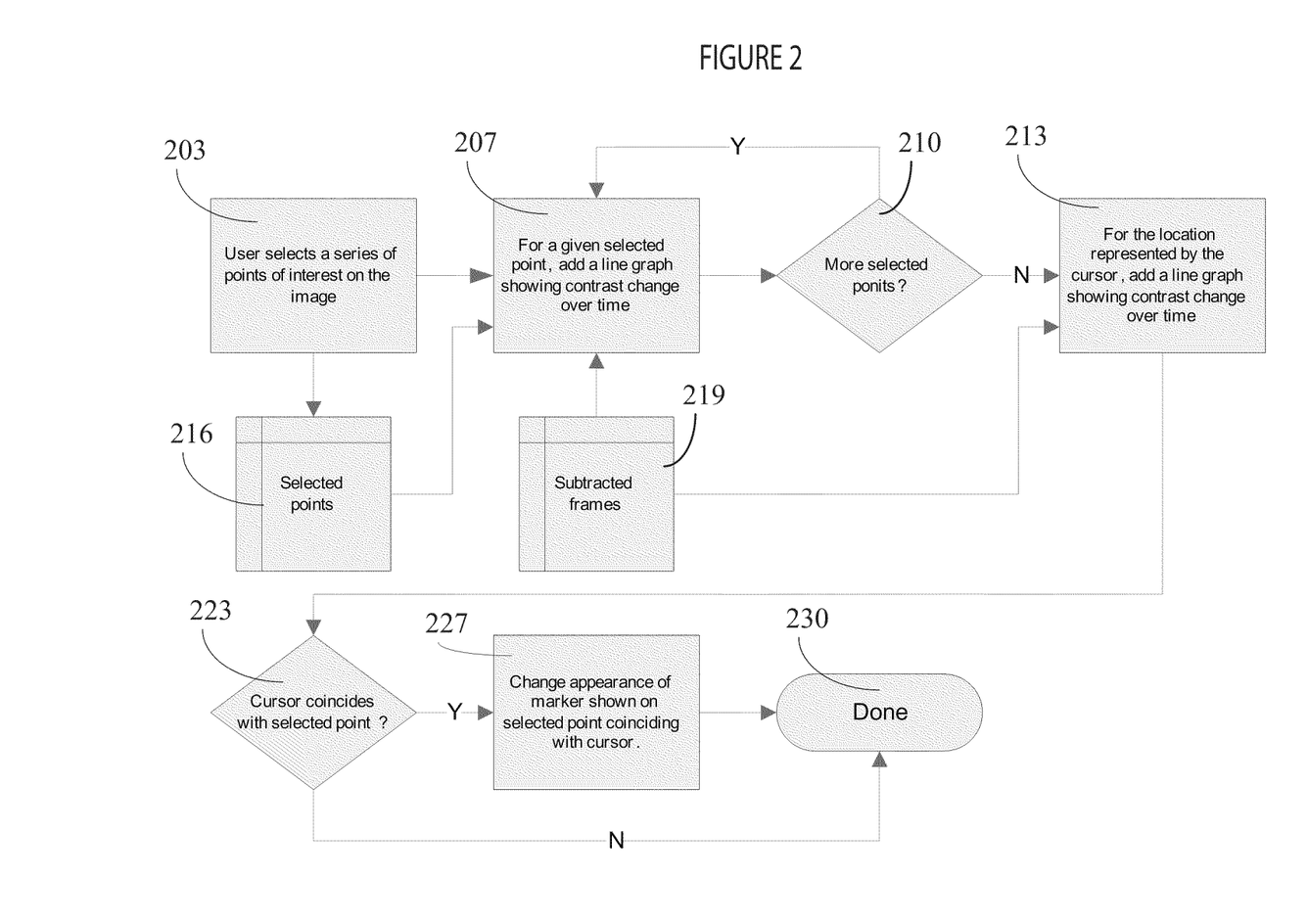
FIG. 2 shows a flowchart of a process for generating a graph of contrast agent concentration in a particular portion of a vessel structure, according to invention principles.

FIG. 2 shows a flowchart of a process used by data processor 29 for generating a graph of contrast agent concentration in a particular portion of a vessel structure in an image. In step 207, data processor 29 automatically generates a graph of contrast agent concentration, over a predetermined period of time, in a particular portion of the vessel structure indicated by a first point of a series of points 216 selected from within a DSA image by a user in step 203. In steps 210 and 207, data processor 29 automatically iteratively generates graphs of contrast agent concentration, over a predetermined period of time, in particular portions of the vessel structure indicated by the remaining points of the series of points 216. In step 213, data processor 29 automatically generates a graph of contrast agent concentration, over a predetermined period of time, in a particular portion of the vessel structure indicated by a cursor within the DSA image.

In step 219, display processor 15 generates data representing a single composite display image including, first and second image areas. The first image area shows the DSA image of the patient vessel structure and contrast agent flow through the patient vessel structure over a predetermined period of time. The second image area shows a graph of contrast agent concentration generated by data processor 29 at a selected point in the vessel structure in the DSA image. Further, in response to data processor 29 determining in step 223, that the cursor of step 213 is coincident in location in the DSA image with a selected point of points 216, display processor 15 in step 227 changes visual appearance of the displayed cursor to indicate the coincidence. The process of FIG. 2 ends at step 230.

Data processor 29 generates a graph of contrast agent intensity (representing blood flow) over time during display of a DSA (digitally subtracted angiography) image, in response to user selection of a point of interest in the DSA image. The graph of contrast agent intensity over time is generated by examining luminance intensity of an individual pixel (or group of pixels) comprising a selected point for each image frame in an acquired image sequence and by plotting luminance intensity of the individual pixel (or group of pixels) against time derived from a timestamp of the corresponding image frame containing the individual pixel.

Figure 3:
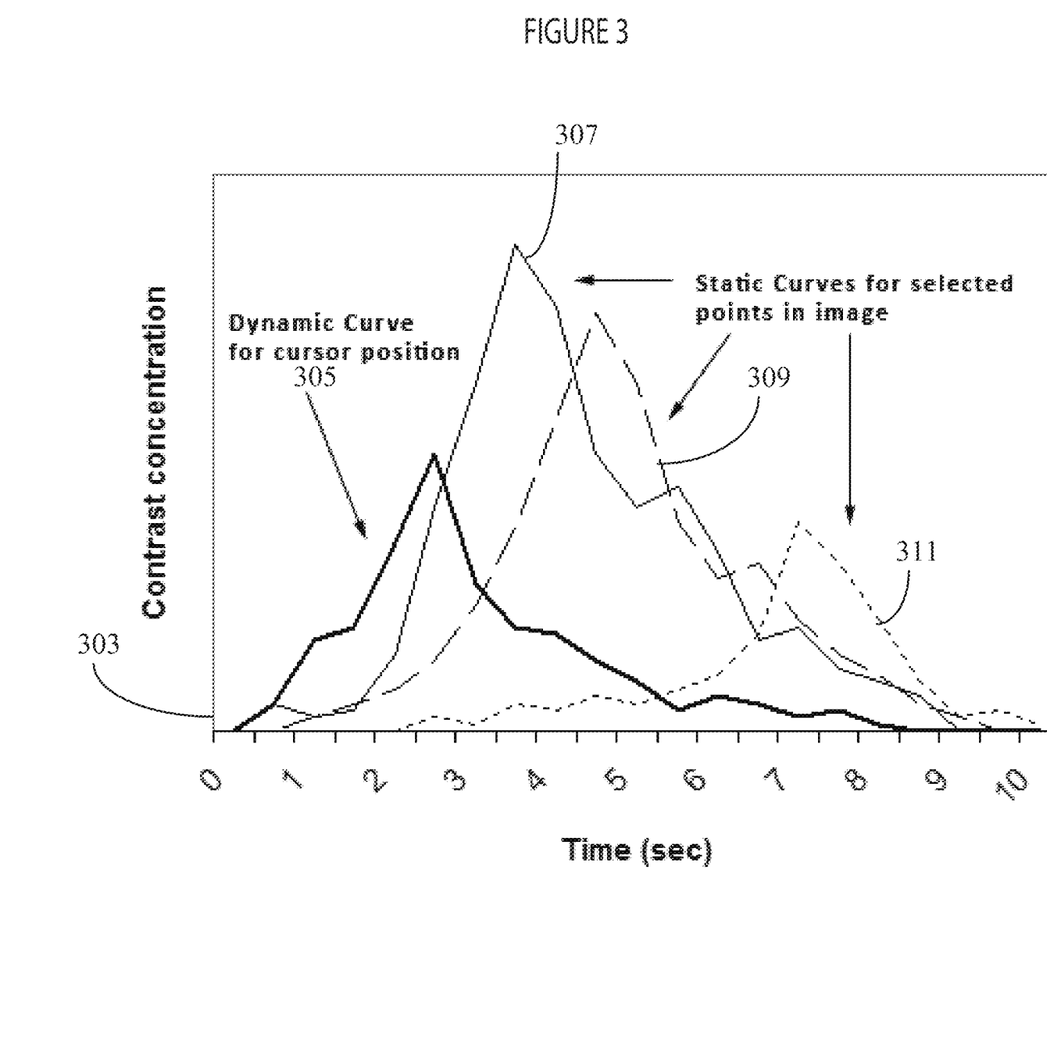
FIG. 3 shows a graph presenting both dynamic and static representations of contrast agent concentration represented by luminance intensity, over time, according to invention principles.

FIG. 3 shows graph 303 presenting both dynamic and static representations of contrast agent concentration represented by luminance intensity over time. The graph is advantageously displayed concurrently with an image of the vasculature in a composite image on display 19 (FIG. 1). A point in vasculature in the displayed image is labelled by user data entry as being selected for a graph and a graph of contrast agent intensity over time is generated by data processor 29 for the selected point. System 10 enables a user to compare contrast agent flow (representing blood flow) at one point in the image with that of one or more other points, in response to user selection of one or more additional points in the image.

Data processor 29 automatically generates multiple curves for the corresponding multiple points and presents the multiple curves in the graph of FIG. 3. In order to differentiate between multiple graphical curves displayed in response to user selection of the multiple points, the curves are displayed in varying colors (or with other differentiating visual attributes hue, shade, shape, dashed line pattern, for example). The colors can either be a function of the data at the point selected (e.g., the color displayed in a static color image such as red for venous flow and blue for arterial flow) in one embodiment or in another embodiment, the colors are assigned by the system to be discernable from other existing curves.

Curves 307, 309 and 311 show contrast agent concentration represented by luminance intensity over time for corresponding static user selected points in the image. Curve 305 shows contrast agent concentration represented by luminance intensity over time for a dynamically movable point comprising a cursor position in the image if it is hovering over the image. This curve is drawn to be distinguishable from other curves initiated in response to user selection of points in the image, and changes with the position of the user cursor (or other interface pointer). If the pointer is positioned on or nearly on a point that has already been selected, both the selected point and the curve corresponding to the point change in appearance to more distinctly indicate the correlation between the point and the curve. This is done by changing curve color (e.g., using a bright color only to draw the highlighted curve) or drawing pattern (e.g., use of a thicker line for the graph or different marker shape for the marker of the selected point) or by using another visual attribute.

Figure 4:
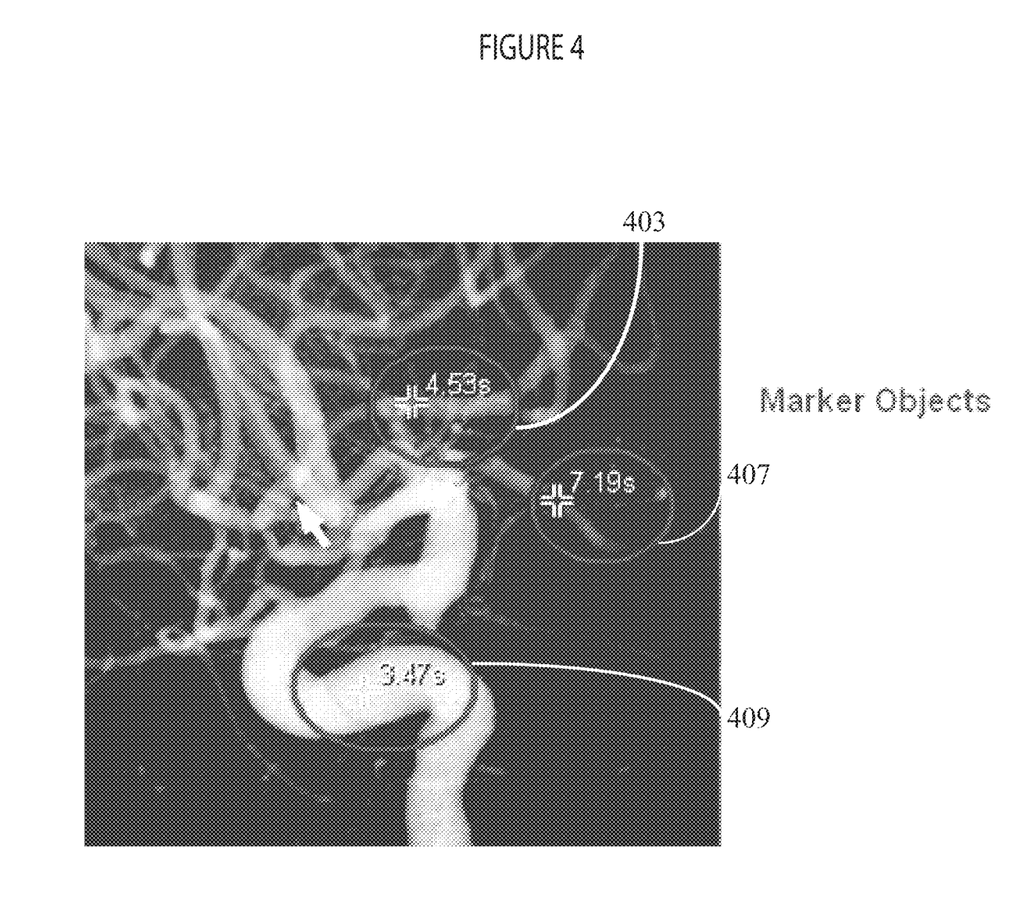
FIG. 4 shows an X-ray image of a vessel structure including marker objects (circled) positioned by a user, according to invention principles.

FIG. 4 shows an X-ray image of a vessel structure including marker objects (circled) positioned by a user identifying different points in corresponding different vessels. Specifically, FIG. 4 shows markers (encircled by circles 403, 407 and 409) selected by user data entry in the image. Data processor 29 automatically generates curves of contrast agent concentration represented by luminance intensity over time of the points identified by the markers for presentation in a single graph concurrently displayed in a single composite image in a first image area together with the image in a second image area.

Figure 5A:
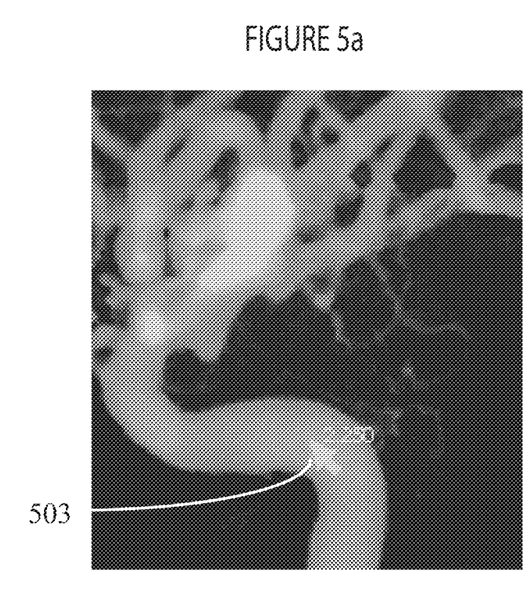
FIGS. 5a and 5b show X-ray images of a vessel structure illustrating elements identifying a cursor position and a cursor position coincident with a marker, respectively, according to invention principles.
Figure 5B:
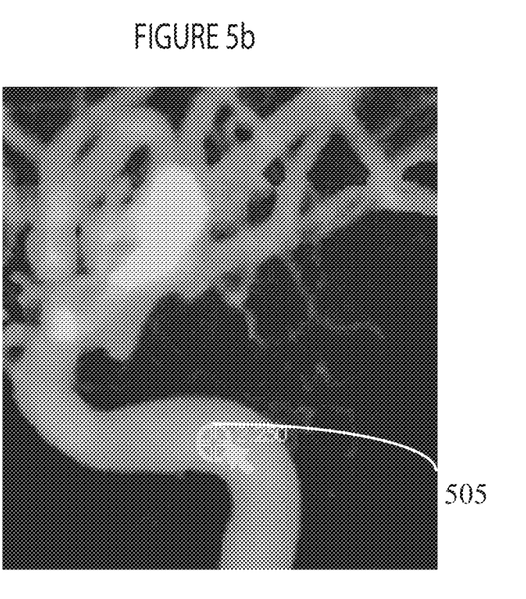

FIGS. 5a and 5b show X-ray images of a vessel structure illustrating elements identifying a cursor position 503 and a cursor position coincident with a marker 505, respectively. In response to data processor 29 (FIG. 1) determining that a cursor is substantially coincident in location in an X-ray image with a selected point, display processor 15 changes appearance of the displayed marker (e.g., by encircling the marker or by using another visual attribute to distinctively identify the marker to indicate the coincidence.

Figure 6:
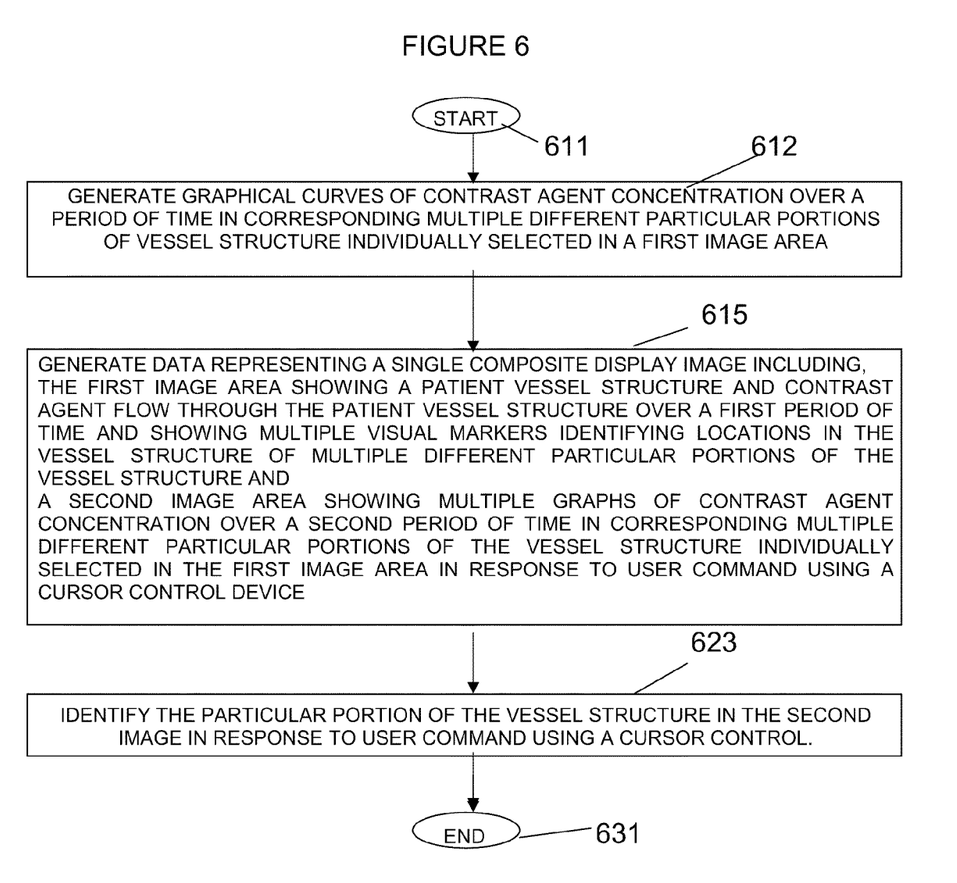
FIG. 6 shows a flowchart of a process used by a system enabling user interaction with a medical vessel structure image to determine individual vessel blood flow characteristics, according to invention principles.

FIG. 6 shows a flowchart of a process used by system 10 enabling user interaction with a medical vessel structure image to determine individual vessel blood flow characteristics. In step 612 following the start at step 611, data processor 29 generates graphical curves of contrast agent concentration over a period of time in corresponding multiple different particular portions of the vessel structure individually selected in a medical vessel structure image. In step 615, display processor 15 generates data representing a single composite display image including first and second image areas. The first image area shows a patient vessel structure and contrast agent flow through the patient vessel structure over a first period of time and shows multiple visual markers identifying locations in the vessel structure of multiple different particular portions of the vessel structure. In one embodiment the first image area is derived by, associating different individual images of multiple digitally subtracted images with different corresponding visual attributes and combining data representing the digitally subtracted images to form an image in the first image area.

A visual marker also includes data indicating a time substantially representing time of peak contrast agent concentration in the particular portion of the vessel structure from introduction of contrast agent into a patient vessel structure. The visual marker also includes data indicating a maximum or minimum rate of change of concentration of contrast agent in the particular portion of the vessel structure from introduction of contrast agent into a patient vessel structure. The visual marker further includes data indicating a time period comprising substantially half way between time of peak contrast agent concentration in the particular portion of the vessel structure from at least one of, (a) time of introduction of contrast agent into a patient vessel structure and (b) time of end of contrast agent flow in the patient vessel structure.

The second image area shows multiple graphical curves of contrast agent concentration over a second period of time in corresponding multiple different particular portions of the vessel structure individually selected in the first image area in response to user command using a cursor control device. In one embodiment, the first period of time and the second period of time are the same. The different portions comprise a first portion selected in the first image area in response to user command and a second portion selected in the first image area in response to a current cursor hover location. In response to the first portion and the second portion comprising the same location in the vessel structure, the first display image displays a unique single marker. The multiple graphs have individually distinguishing visual attributes comprising at least one of, (a) color, (b) line pattern, (c) shade, (d) hue and (e) brightness. The multiple visual markers correspond to the multiple graphs. The second image area shows a visual marker indicating a time substantially representing time of peak contrast agent concentration in the particular portion of the vessel structure from introduction of contrast agent into a patient vessel structure. The second image area also shows a visual marker indicating a maximum or minimum rate of change of concentration of contrast agent in the particular portion of the vessel structure from introduction of contrast agent into a patient vessel structure. The second image area further shows a visual marker indicating a time period comprising substantially half way between time of peak contrast agent concentration in the particular portion of the vessel structure from at least one of, (a) time of introduction of contrast agent into a patient vessel structure and (b) time of end of contrast agent flow in the patient vessel structure.

In step 623 display processor 15 identifies the particular portion of the vessel structure in the second image in response to user command using a cursor control. The individual markers of the multiple visual markers share a visual attribute with a corresponding graph of the multiple graphs enabling unique matching of a graph with a corresponding marker and particular portion of the vessel structure. The process of FIG. 6 terminates at step 631.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A display processor or generator is a known element comprising electronic circuitry or software or a combination of both for generating display images or portions thereof.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-6 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system enables a user to visualize and compare blood flow characteristics over time at selected points in an angiographic X-ray image through a generated graph of contrast agent intensity over time, in response to user selection of a point of interest in the image. Further, the processes and applications may, in alternative embodiments, be located on one or more (e.g., distributed) processing devices on the network of FIG. 1. Any of the functions and steps provided in FIGS. 1-6 may be implemented in hardware, software or a combination of both.

What is claimed is:

1. A system and user interface enabling user interaction with a medical vessel structure image to determine individual vessel blood flow characteristics, comprising:
 a user interface cursor control device; and
 a display processor for generating data representing a single composite display image including,
  a first image area showing a patient vessel structure and contrast agent flow through said patient vessel structure over a first period of time and
  a second image area showing a dynamic curve graph of contrast agent concentration in a particular portion of said vessel structure over a second period of time, said particular portion of said vessel structure comprising one or a group of pixels corresponding to a dynamically movable cursor hovering over said first image area in said vessel structure shown in said first image area and being moved in response to a user using said cursor control device, said first image area showing a visual marker identifying location in said vessel structure of said dynamically movable cursor of said vessel structure in said first image area, wherein the dynamic curve graph changes with the location of said dynamically movable cursor.

2. A system according to claim 1, wherein
said image in said first image area comprises a DSA (digitally subtracted angiography) image derived by subtracting a mask image acquired in the absence of contrast agent, from subsequent images acquired when a contrast agent is in patient blood to remove static background detail.

3. A system according to claim 1, wherein
said visual marker also includes data indicating a time substantially representing time of peak contrast agent concentration in said particular portion of said vessel structure from introduction of contrast agent into a patient vessel structure and including a data processor for deriving said graph by examining luminance intensity of said one or said group of pixels comprising a selected point for each image frame in an acquired image sequence and by plotting luminance intensity of the individual pixel (or group of pixels) against time derived from a timestamp of the corresponding image frame containing the individual pixel.

4. A system according to claim 1, wherein
said visual marker also includes data indicating a maximum or minimum rate of change of concentration of contrast agent in said particular portion of said vessel structure from introduction of contrast agent into a patient vessel structure.

5. A system according to claim 1, wherein
said visual marker also includes data indicating a time period comprising substantially half way between time of peak contrast agent concentration in said particular portion of said vessel structure from at least one of (a) time of introduction of contrast agent into a patient vessel structure and (b) time of end of contrast agent flow in said patient vessel structure.

6. A system according to claim 1, wherein
said second image area shows a visual marker indicating a time substantially representing time of peak contrast agent concentration in said particular portion of said vessel structure from introduction of contrast agent into a patient vessel structure.

7. A system according to claim 1, wherein
said second image area shows a visual marker indicating a maximum or minimum rate of change of concentration of contrast agent in said particular portion of said vessel structure from introduction of contrast agent into a patient vessel structure.

8. A system according to claim 1, wherein
said second image area shows a visual marker indicating a time period comprising substantially half way between time of peak contrast agent concentration in said particular portion of said vessel structure from at least one of, (a) time of introduction of contrast agent into a patient vessel structure and (b) time of end of contrast agent flow in said patient vessel structure.

9. A system according to claim 1, wherein
said second image area shows a plurality of graphs of contrast agent concentration over said second period of time in a corresponding plurality of different particular portions of said vessel structure individually selected in said first image area in response to the user using said cursor control device and
said first image area shows a plurality of visual markers corresponding to said plurality of graphs identifying locations in said vessel structure of said plurality of different particular portions of said vessel structure.

10. A system according to claim 9, wherein
said plurality of graphs have individually distinguishing visual attributes comprising at least one of, (a) color, (b) line pattern, (c) shade, (d) hue and (e) brightness.

11. A system according to claim 10, wherein
an individual marker of said plurality of visual markers shares a visual attribute with a corresponding graph of said plurality of graphs enabling unique matching of a graph with a corresponding marker and particular portion of said vessel structure.

12. A system according to claim 1, wherein
said second image area shows the dynamic curve graph and at least one static curve graph of contrast agent concentration in a corresponding plurality of different particular portions of said vessel structure, the corresponding plurality of different portions comprising a first portion selected in said first image area corresponding to the dynamically movable cursor and a second portion selected in said first image area corresponding to a static user selected point, the dynamic curve graph and the static curve graph enabling the user to compare contrast agent flow at one dynamically movable cursor in said vessel structure with that of another static user selected point in said vessel structure and
said first image area shows a plurality of visual markers corresponding to the dynamic curve graph and the static graph identifying locations in said vessel structure of said plurality of different particular portions of said vessel structure.

13. A system according to claim 12, wherein
in response to said first portion and said second portion comprising the same location in said vessel structure, said first display image displays a unique single marker.

14. A system according to claim 1, wherein
said first image area showing contrast agent flow through a patient vessel structure over a first period of time is derived by,
 associating different individual images of a plurality of digitally subtracted images with different corresponding visual attributes and
 combining data representing said digitally subtracted images to form an image in said first image area.

15. A system according to claim 1, wherein
said first period of time and said second period of time are the same.

16. A method enabling user interaction with a medical vessel structure image to determine individual vessel blood flow characteristics, comprising the activities of:
    generating data representing a single composite display image including,
        a first image area showing a patient vessel structure and contrast agent flow through said patient vessel structure over a first period of time and showing a visual marker identifying location in said vessel structure of a particular portion of said vessel structure comprising one or a group of pixels corresponding to a dynamically movable cursor hovering over said first image area and in said vessel structure and
        a second image area showing a dynamic curve graph of contrast agent concentration of said one or said group of pixels of said particular portion of said vessel structure over a second period of time, wherein the dynamic curve graph changes with the location of the dynamically movable cursor; and
    identifying said particular portion of said vessel structure in said second image in response to a user using a cursor control.

17. A method according to claim 16, wherein
said visual marker also includes data indicating a time substantially representing time of peak contrast agent concentration in said particular portion of said vessel structure from introduction of contrast agent into a patient vessel structure.

18. A method enabling user interaction with a medical vessel structure image to determine individual vessel blood flow characteristics, comprising the activities of:
    generating data representing a single composite display image including,
        a first image area showing a patient vessel structure and contrast agent flow through said patient vessel structure over a first period of time and showing a plurality of visual markers identifying locations in said vessel structure of a plurality of different particular portions of said vessel structure and
        a second image area showing at least one dynamic curve graph and at least one static curve graph of contrast agent concentration over a second period of time in a corresponding plurality of different particular portions of said vessel structure, the corresponding plurality of different portions are individually selected in said first image area in response to a user using a cursor control device and correspond to a dynamically movable cursor hovering over said first image area and a static user selected point, said plurality of visual markers corresponding to said curve graphs, said curve graphs enabling the user to compare contrast agent flow at one dynamically movable cursor in said vessel structure with that of one or more other static user selected points in said vessel structure, said dynamic curve graph changes with location of the dynamically movable cursor; and
    identifying said particular portion of said vessel structure in said second image in response to the user using a cursor control.

19. A method according to claim 18, wherein individual markers of said plurality of visual markers share a visual attribute with a corresponding graph of said graphs enabling unique matching of a graph with a corresponding marker and particular portion of said vessel structure.

20. A method according to claim 18, including the activity of
    generating graphs of contrast agent concentration over a second period of time in said corresponding plurality of different particular portions of said vessel structure individually selected in a medical vessel structure image.

\* \* \* \* \*